(12) United States Patent
Bailey (10) Patent No.: US 9,615,562 B2
(45) Date of Patent: Apr. 11, 2017

(54) ANALYZING MARINE TRIP DATA

(71) Applicant: Navico Holding AS, Egersund (NO)

(72) Inventor: Paul Robert Bailey, Auckland (NZ)

(73) Assignee: NAVICO HOLDING AS, Egersund (NO)

( * ) Notice: Subject to any disclaimer, the term of this patent is extended or adjusted under 35 U.S.C. 154(b) by 9 days.

(21) Appl. No.: 14/461,349

(22) Filed: Aug. 15, 2014

(65) Prior Publication Data

US 2015/0057929 A1    Feb. 26, 2015

Related U.S. Application Data

(60) Provisional application No. 61/868,444, filed on Aug. 21, 2013.

(51) Int. Cl.
*G01C 21/20* (2006.01)
*A01K 97/00* (2006.01)
(Continued)

(52) U.S. Cl.
CPC .............. *A01K 97/00* (2013.01); *A01K 79/00* (2013.01); *A01K 99/00* (2013.01); *A61B 5/1118* (2013.01); *A61B 5/1123* (2013.01); *G01B 21/00* (2013.01); *G01C 21/20* (2013.01); *G01C 21/203* (2013.01); *G06F 3/014* (2013.01); *G06F 3/017* (2013.01);
(Continued)

(58) Field of Classification Search
CPC .... A01K 97/00; A01K 79/00; H04N 21/4335; H04N 5/91; H04N 5/232; G01C 21/203; H04Q 9/00; G08C 17/02; G01B 21/00; G11B 27/031; G06F 11/3438; G06F 11/3476; G06F 3/017; G06F 17/30867; G06T 7/209
See application file for complete search history.

(56) References Cited

U.S. PATENT DOCUMENTS 4,829,493 A    5/1989   Bailey
4,879,697 A    11/1989  Lowrance et al.
(Continued)

FOREIGN PATENT DOCUMENTS

DE    102004059619 A1   6/2006
EP       1561377 A1     8/2005
(Continued)

OTHER PUBLICATIONS

PCT International Search Report and Written Opinion; PCT/IB2014/063979; Jan. 7, 2015.
(Continued)

*Primary Examiner* — Adam Mott
(74) *Attorney, Agent, or Firm* — Nelson Mullins Riley & Scarborough LLP (57) ABSTRACT

Various implementations described herein are directed to a non-transitory computer readable medium having stored thereon computer-executable instructions which, when executed by a computer, may cause the computer to receive data recorded by a wearable device during a fishing trip. The computer may receive location data that corresponds to the fishing trip. The computer may use the data recorded by the wearable device to determine a time period for a fishing activity during the fishing trip. The computer may use the location data to determine locations corresponding to the time period.

19 Claims, 6 Drawing Sheets

(51) Int. Cl.

| | | |
|---|---|---|
| *H04N 5/232* | (2006.01) | |
| *H04N 5/91* | (2006.01) | |
| *H04N 21/4335* | (2011.01) | |
| *G08C 17/02* | (2006.01) | |
| *G06F 3/01* | (2006.01) | |
| *G06F 3/023* | (2006.01) | |
| *G06F 15/02* | (2006.01) | |
| *G06T 11/20* | (2006.01) | |
| *G06T 7/20* | (2017.01) | |
| *G06T 7/60* | (2017.01) | |
| *G11B 27/031* | (2006.01) | |
| *G11B 27/17* | (2006.01) | |
| *G11B 31/00* | (2006.01) | |
| *A01K 99/00* | (2006.01) | |
| *A61B 5/11* | (2006.01) | |
| *G01B 21/00* | (2006.01) | |
| *G06Q 10/00* | (2012.01) | |
| *G06Q 50/00* | (2012.01) | |
| *G06F 17/30* | (2006.01) | |
| *A01K 79/00* | (2006.01) | |
| *G06F 11/34* | (2006.01) | |
| *G06K 9/00* | (2006.01) | |
| *G11B 27/28* | (2006.01) | |
| *G11B 27/34* | (2006.01) | |
| *G06F 3/0346* | (2013.01) | |
| *H04Q 9/00* | (2006.01) | |
| *B63B 49/00* | (2006.01) | |
| *G01S 15/96* | (2006.01) | |
| *G06F 11/30* | (2006.01) | |
| *G01S 7/00* | (2006.01) | |

(52) U.S. Cl.
CPC .......... *G06F 3/0231* (2013.01); *G06F 3/0346* (2013.01); *G06F 11/3438* (2013.01); *G06F 11/3476* (2013.01); *G06F 15/0225* (2013.01); *G06F 17/30867* (2013.01); *G06K 9/00342* (2013.01); *G06Q 10/00* (2013.01); *G06Q 50/01* (2013.01); *G06T 7/2033* (2013.01); *G06T 7/2093* (2013.01); *G06T 7/60* (2013.01); *G06T 11/206* (2013.01); *G08C 17/02* (2013.01); *G11B 27/031* (2013.01); *G11B 27/17* (2013.01); *G11B 27/28* (2013.01); *G11B 27/34* (2013.01); *G11B 31/006* (2013.01); *H04N 5/232* (2013.01); *H04N 5/91* (2013.01); *H04N 21/4335* (2013.01); *H04Q 9/00* (2013.01); *B63B 49/00* (2013.01); *G01S 7/003* (2013.01); *G01S 15/96* (2013.01); *G06F 11/3013* (2013.01); *G06F 11/3058* (2013.01); *G06F 2201/835* (2013.01); *G06T 2207/10016* (2013.01); *G06T 2207/30196* (2013.01); *G08C 2201/32* (2013.01); *H04Q 2209/43* (2013.01); *Y02B 60/165* (2013.01)

(56) References Cited

U.S. PATENT DOCUMENTS

| | | | |
|---|---|---|---|
| 5,025,423 A | 6/1991 | Earp | |
| 5,191,341 A | 3/1993 | Gouard et al. | |
| 5,321,391 A | 6/1994 | Fox | |
| 5,446,775 A | 8/1995 | Wright et al. | |
| 5,537,380 A | 7/1996 | Sprankle, Jr. et al. | |
| 5,546,695 A | 8/1996 | Langer | |
| 6,222,449 B1 | 4/2001 | Twining | |
| 6,225,984 B1 | 5/2001 | Crawford | |
| 6,252,544 B1 | 6/2001 | Hoffberg | |
| 6,263,147 B1 | 7/2001 | Tognazzini | |
| 6,321,158 B1 | 11/2001 | DeLorme et al. | |
| 6,411,283 B1 | 6/2002 | Murphy | |
| 6,418,080 B2 | 7/2002 | Inouchi | |
| 6,421,299 B1 | 7/2002 | Betts et al. | |
| 6,459,372 B1 | 10/2002 | Branham et al. | |
| 6,567,792 B1 | 5/2003 | Arnold | |
| 6,584,722 B1 * | 7/2003 | Walls | A01K 97/00 377/5 |
| 6,587,740 B2 | 7/2003 | Byrne et al. | |
| 6,751,626 B2 * | 6/2004 | Brown | G06Q 10/06 |
| 6,761,692 B2 | 7/2004 | Angelsen et al. | |
| 6,798,378 B1 | 9/2004 | Walters | |
| 6,816,782 B1 | 11/2004 | Walters et al. | |
| 7,002,579 B2 | 2/2006 | Olson | |
| 7,236,426 B2 | 6/2007 | Turner et al. | |
| 7,243,457 B1 | 7/2007 | Smith et al. | |
| 7,319,992 B1 | 1/2008 | Gaos | |
| 7,321,824 B1 * | 1/2008 | Nesbitt | G01C 21/367 340/955 |
| 7,430,461 B1 | 9/2008 | Michaels | |
| 7,652,952 B2 | 1/2010 | Betts et al. | |
| 7,710,825 B2 | 5/2010 | Betts et al. | |
| 7,722,218 B2 | 5/2010 | Leung | |
| 7,729,203 B2 | 6/2010 | Betts et al. | |
| 7,755,974 B2 | 7/2010 | Betts et al. | |
| 7,812,667 B2 | 10/2010 | Fagg | |
| 7,870,496 B1 | 1/2011 | Sherwani | |
| 7,890,867 B1 | 2/2011 | Margulis | |
| 8,019,532 B2 | 9/2011 | Sheha et al. | |
| 8,040,758 B1 | 10/2011 | Dickinson | |
| 8,063,540 B2 | 11/2011 | Angelsen et al. | |
| 2001/0054961 A1 | 12/2001 | Twining | |
| 2002/0035574 A1 | 3/2002 | Dumas | |
| 2002/0093541 A1 | 7/2002 | Schileru-Key | |
| 2002/0099457 A1 | 7/2002 | Fredlund et al. | |
| 2003/0046689 A1 | 3/2003 | Gaos | |
| 2003/0056419 A1 | 3/2003 | Squires et al. | |
| 2003/0089020 A1 | 5/2003 | Dirito | |
| 2004/0124297 A1 | 7/2004 | Steer | |
| 2004/0162830 A1 | 8/2004 | Shirwadkar et al. | |
| 2004/0193364 A1 | 9/2004 | Chojnacki | |
| 2004/0249860 A1 * | 12/2004 | Stechschulte | A01K 97/00 |
| 2005/0037872 A1 | 2/2005 | Fredlund et al. | |
| 2005/0102101 A1 | 5/2005 | Beesley et al. | |
| 2006/0013066 A1 | 1/2006 | Nishimori et al. | |
| 2006/0048434 A1 | 3/2006 | Congel | |
| 2006/0119585 A1 | 6/2006 | Skinner | |
| 2006/0224940 A1 | 10/2006 | Lee | |
| 2006/0265931 A1 | 11/2006 | McFadden et al. | |
| 2007/0011334 A1 | 1/2007 | Higgins et al. | |
| 2007/0045010 A1 | 3/2007 | Kasperek | |
| 2007/0058489 A1 | 3/2007 | Bratcher | |
| 2007/0220798 A1 | 9/2007 | Davidson | |
| 2008/0126935 A1 | 5/2008 | Blomgren | |
| 2008/0165022 A1 | 7/2008 | Herz et al. | |
| 2008/0204424 A1 | 8/2008 | Jin et al. | |
| 2008/0246627 A1 | 10/2008 | Guazzelli | |
| 2009/0064055 A1 | 3/2009 | Chaudhri et al. | |
| 2009/0099871 A1 | 4/2009 | Gadodia | |
| 2009/0105952 A1 | 4/2009 | Grace et al. | |
| 2009/0179789 A1 | 7/2009 | Haughay, Jr. et al. | |
| 2009/0240354 A1 | 9/2009 | Davidson | |
| 2009/0241636 A1 | 10/2009 | Obori | |
| 2009/0249247 A1 | 10/2009 | Tseng et al. | |
| 2009/0258710 A1 | 10/2009 | Quatrochi | |
| 2009/0271054 A1 | 10/2009 | Dokken | |
| 2009/0287409 A1 | 11/2009 | Summers | |
| 2009/0295626 A1 | 12/2009 | Su | |
| 2010/0049468 A1 | 2/2010 | Papadourakis | |
| 2010/0080082 A1 | 4/2010 | Betts et al. | |
| 2010/0145601 A1 | 6/2010 | Kurtti et al. | |
| 2010/0199225 A1 | 8/2010 | Coleman et al. | |
| 2010/0226203 A1 | 9/2010 | Buttle et al. | |
| 2010/0250122 A1 | 9/2010 | Kubota et al. | |
| 2011/0007035 A1 | 1/2011 | Shai | |
| 2011/0013484 A1 | 1/2011 | Coleman et al. | |
| 2011/0013485 A1 | 1/2011 | Maguire | |
| 2011/0019887 A1 | 1/2011 | Roehrig et al. | |
| 2011/0025720 A1 | 2/2011 | Jo et al. | |

(56) References Cited

U.S. PATENT DOCUMENTS

| | | | |
|---|---|---|---|
| 2011/0082644 A1* | 4/2011 | Imasaka | A01K 97/00 701/494 |
| 2011/0154183 A1 | 6/2011 | Burns et al. | |
| 2011/0208479 A1 | 8/2011 | Chaves | |
| 2011/0213515 A1 | 9/2011 | Haymart et al. | |
| 2011/0214500 A1 | 9/2011 | Cabrera et al. | |
| 2011/0257819 A1 | 10/2011 | Chen et al. | |
| 2012/0001773 A1 | 1/2012 | Lyons et al. | |
| 2012/0011437 A1 | 1/2012 | James et al. | |
| 2012/0014220 A1 | 1/2012 | DePasqua | |
| 2012/0047790 A1 | 3/2012 | Hess et al. | |
| 2012/0069712 A1 | 3/2012 | Potanin et al. | |
| 2012/0106300 A1 | 5/2012 | Maguire | |
| 2012/0144384 A1 | 6/2012 | Baek | |
| 2012/0144723 A1 | 6/2012 | Davidson | |
| 2012/0185801 A1 | 7/2012 | Madonna et al. | |
| 2012/0316456 A1 | 12/2012 | Rahman et al. | |
| 2012/0317167 A1 | 12/2012 | Rahman et al. | |
| 2013/0007665 A1 | 1/2013 | Chaudhri et al. | |
| 2013/0040714 A1 | 2/2013 | Rosing | |
| 2013/0074051 A1 | 3/2013 | Freeman | |
| 2013/0096575 A1 | 4/2013 | Olson | |
| 2013/0107031 A1 | 5/2013 | Atkinson | |
| 2013/0281087 A1 | 10/2013 | Ruhanen et al. | |
| 2013/0307720 A1 | 11/2013 | Lilburn | |
| 2013/0343151 A1* | 12/2013 | Shiraki | G01S 15/96 367/7 |
| 2014/0012587 A1 | 1/2014 | Park | |
| 2014/0032468 A1 | 1/2014 | Anandaraj | |
| 2014/0071059 A1 | 3/2014 | Girault | |
| 2014/0111368 A1 | 4/2014 | Lee et al. | |
| 2014/0180566 A1 | 6/2014 | Malhotra | |
| 2014/0195297 A1 | 7/2014 | Abuelsaad et al. | |
| 2014/0358483 A1 | 12/2014 | da Rosa | |
| 2015/0019135 A1 | 1/2015 | Kacyvenski | |
| 2015/0051786 A1 | 2/2015 | Wang | |
| 2015/0054655 A1 | 2/2015 | Bailey et al. | |
| 2015/0054732 A1 | 2/2015 | Bailey | |
| 2015/0054828 A1 | 2/2015 | Bailey | |
| 2015/0054829 A1 | 2/2015 | Bailey | |
| 2015/0055827 A1 | 2/2015 | Bailey | |
| 2015/0055930 A1 | 2/2015 | Bailey | |
| 2015/0057929 A1 | 2/2015 | Bailey | |
| 2015/0057965 A1 | 2/2015 | Gaynor | |
| 2015/0057968 A1 | 2/2015 | Bailey | |
| 2015/0058020 A1 | 2/2015 | Bailey | |
| 2015/0058237 A1 | 2/2015 | Bailey | |
| 2015/0058323 A1 | 2/2015 | Bailey | |
| 2015/0310524 A1 | 10/2015 | Gospodarek et al. | |
| 2016/0125348 A1 | 5/2016 | Dyer et al. | |

FOREIGN PATENT DOCUMENTS

| | | |
|---|---|---|
| EP | 2613223 A1 | 7/2013 |
| JP | 2004207812 A | 7/2004 |
| JP | 2006-158239 A | 6/2006 |
| JP | 2010193284 A | 9/2010 |
| JP | 2011139647 A | 7/2011 |
| WO | 9802037 A1 | 1/1998 |
| WO | 2004088572 A1 | 10/2004 |
| WO | 2010056392 A1 | 5/2010 |
| WO | 2012170163 | 12/2012 |
| WO | 2014088508 A1 | 6/2014 |
| ZA | 2003-08052 A | 7/2004 |

OTHER PUBLICATIONS

PCT International Search Report and Written Opinion; PCT/IB2014/063980; Jan. 5, 2015.
PCT International Search Report and Written Opinion; PCT/IB2014/063982; Dec. 22, 2014.
PCT International Search Report and Written Opinion; PCT/IB2014/063975; Dec. 3, 2014.
PCT International Search Report and Written Opinion; PCT/IB2014/063974; Dec. 2, 2014.
Allen, et al.; Upper Extremity Kinematic Trends of Fly-Casting; Establishing the Effects of Line Length; Sports Biomechanics; vol. 7, No. 1; Jan. 1, 2008; pp. 38-53.
First look at new Mio Link ANT +/Bluetooth Smart optical heart rate wrist band; http://www.dcrainmaker.com/2014/01/mio-link-first-look.html; Jan. 6, 2014 (accessed Apr. 19, 2016).
SAS, "SAS BI Dashboard 4.31 User's Guide", Second Edition, by SAS Electronic book, Aug. 1, 2012, downloaded at http://support.sas.com/documentation/cdl/en/bidbrdug/ 65580/PDF/default/bidrdrug.pdf.
PCT International Search Report and Written Opinion; PCT/IB2013/060285, dated Feb. 18, 2014.
PCT International Search Report and Written Opinion; PCT/IB2014/063976, dated Dec. 12, 2014.
PCT International Search Report and Written Opinion; PCT/IB2014/063983, dated Mar. 5, 2015.
PCT International Search Report and Written Opinion; PCT/US2013/047645, dated Sep. 27, 2013.
PCT International Search Report and Written Opinion; PCT/US2013/047869, dated Oct. 21, 2013.
PCT International Search Report and Written Opinion; PCT/US2013/047926, dated Oct. 11, 2013.
PCT International Search Report and Written Opinion; PCT/US2013/048129, dated Oct. 17, 2013.
PCT International Search Report and Written Opinion; PCT/US2013/048177, dated Oct. 21, 2013.
PCT International Search Report and Written Opinion; PCT/IB2014/063973, dated Nov. 28, 2014.
PCT International Search Report and Written Opinion; PCT/IB2014/063981, dated Feb. 10, 2015.
PCT International Search Report and Written Opinion; PCT/IB2014/063978, dated Dec. 19, 2014.
PCT International Search Report and Written Opinion; PCT/IB2014/063977, dated Nov. 28, 2014.

* cited by examiner

ANALYZING MARINE TRIP DATA

CROSS-REFERENCE TO RELATED APPLICATIONS

This application claims the benefit of U.S. Provisional Patent Application Ser. No. 61/868,444, filed Aug. 21, 2013 and titled FISHING DATA COLLECTION AND USE, the disclosure of which is incorporated herein by reference.

BACKGROUND

This section is intended to provide background information to facilitate a better understanding of various technologies described herein. As the section's title implies, this is a discussion of related art. That such art is related in no way implies that it is prior art. The related art may or may not be prior art. It should therefore be understood that the statements in this section are to be read in this light, and not as admissions of prior art.

Reviewing data captured during a marine trip can be very useful for a fisherman or sailor. Raw data may be captured by various sensors and systems on a vessel during a marine trip. The data may be reviewed in real time, during a trip, or after the trip is complete. By reviewing the data, a fisherman or sailor may be able to improve their performance.

SUMMARY

Described herein are implementations of various technologies for a method for using data recorded by a wearable device to determine a time period for a fishing activity. In one implementation, a non-transitory computer-readable medium having stored thereon computer-executable instructions which, when executed by a computer, cause the computer to perform various actions. The actions may include receiving data recorded by a wearable device during a fishing trip. The actions may include receiving location data that corresponds to the fishing trip. The actions may include using the data recorded by the wearable device to determine a time period for a fishing activity during the fishing trip. The actions may also include using the location data to determine locations corresponding to the time period.

Described herein are also implementations of various technologies for a method for using sonar data to determine a time period for a fishing activity. In one implementation, a non-transitory computer-readable medium having stored thereon computer-executable instructions which, when executed by a computer, cause the computer to perform various actions. The actions may include receiving sonar data recorded during a fishing trip. The actions may include receiving location data that corresponds to the fishing trip. The actions may include using the sonar data to determine a time period for a fishing activity during the fishing trip. The actions may also include using the location data to determine locations corresponding to the time period.

Described herein are also implementations of various technologies for a method for determining time periods in which a fisherman was running, time periods in which the fisherman was finding fish, and time periods in which the fisherman was fishing. In one implementation, a non-transitory computer-readable medium having stored thereon computer-executable instructions which, when executed by a computer, cause the computer to perform various actions. The actions may include receiving data recorded during a fishing trip, where the data include location data, speed and engine data, sonar data, data recorded by a wearable device, or combinations thereof. The actions may include determining at least one time period in which a fisherman was running using the received data. The actions may include determining at least one time period in which the fisherman was finding fish using the received data. The actions may also include determining at least one time period in which the fisherman was fishing using the received data.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various techniques will hereafter be described with reference to the accompanying drawings. It should be understood, however, that the accompanying drawings illustrate only the various implementations described herein and are not meant to limit the scope of various techniques described herein.

DETAILED DESCRIPTION

The discussion below is directed to certain specific implementations. It is to be understood that the discussion below is only for the purpose of enabling a person with ordinary skill in the art to make and use any subject matter defined now or later by the patent "claims" found in any issued patent herein.

It is specifically intended that the claimed invention not be limited to the implementations and illustrations contained herein, but include modified forms of those implementations including portions of the implementations and combinations of elements of different implementations as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the claimed invention unless explicitly indicated as being "critical" or "essential."

Reference will now be made in detail to various implementations, examples of which are illustrated in the accompanying drawings and figures. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the invention. The first object or step, and the second object or step, are both objects or steps, respectively, but they are not to be considered the same object or step.

The terminology used in the description of the present disclosure herein is for the purpose of describing particular implementations only and is not intended to be limiting of the present disclosure. As used in the description of the present disclosure and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context. As used herein, the terms "up" and "down"; "upper" and "lower"; "upwardly" and "downwardly"; "below" and "above"; and other similar terms indicating relative positions above or below a given point or element may be used in connection with some implementations of various technologies described herein.

Various implementations of analyzing marine trip data described herein will now be described in more detail with reference to FIGS. 1-7.

Figure 1:
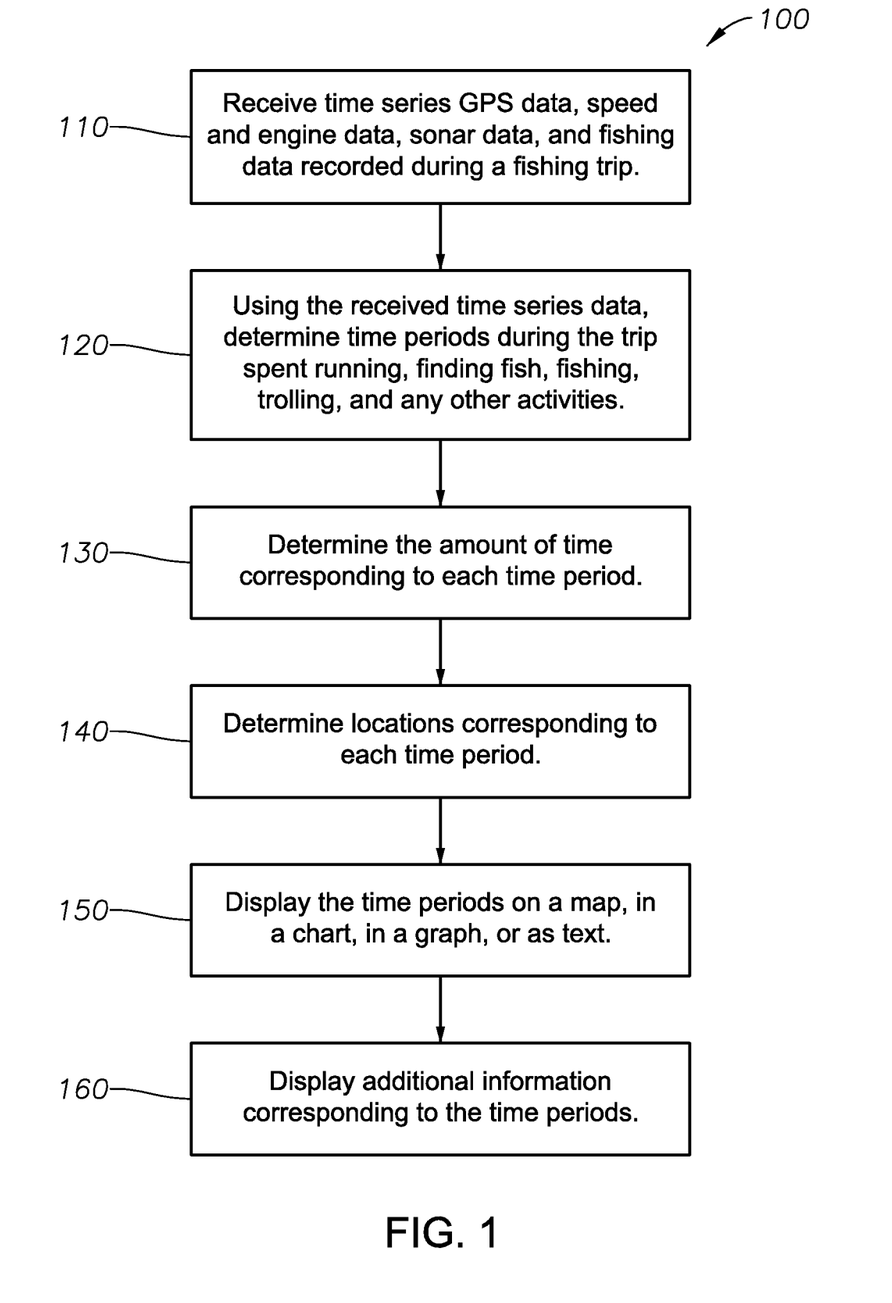
FIG. 1 illustrates a flow diagram of a method for analyzing data recorded during a fishing trip in accordance with implementations of various techniques described herein.
Figure 6:
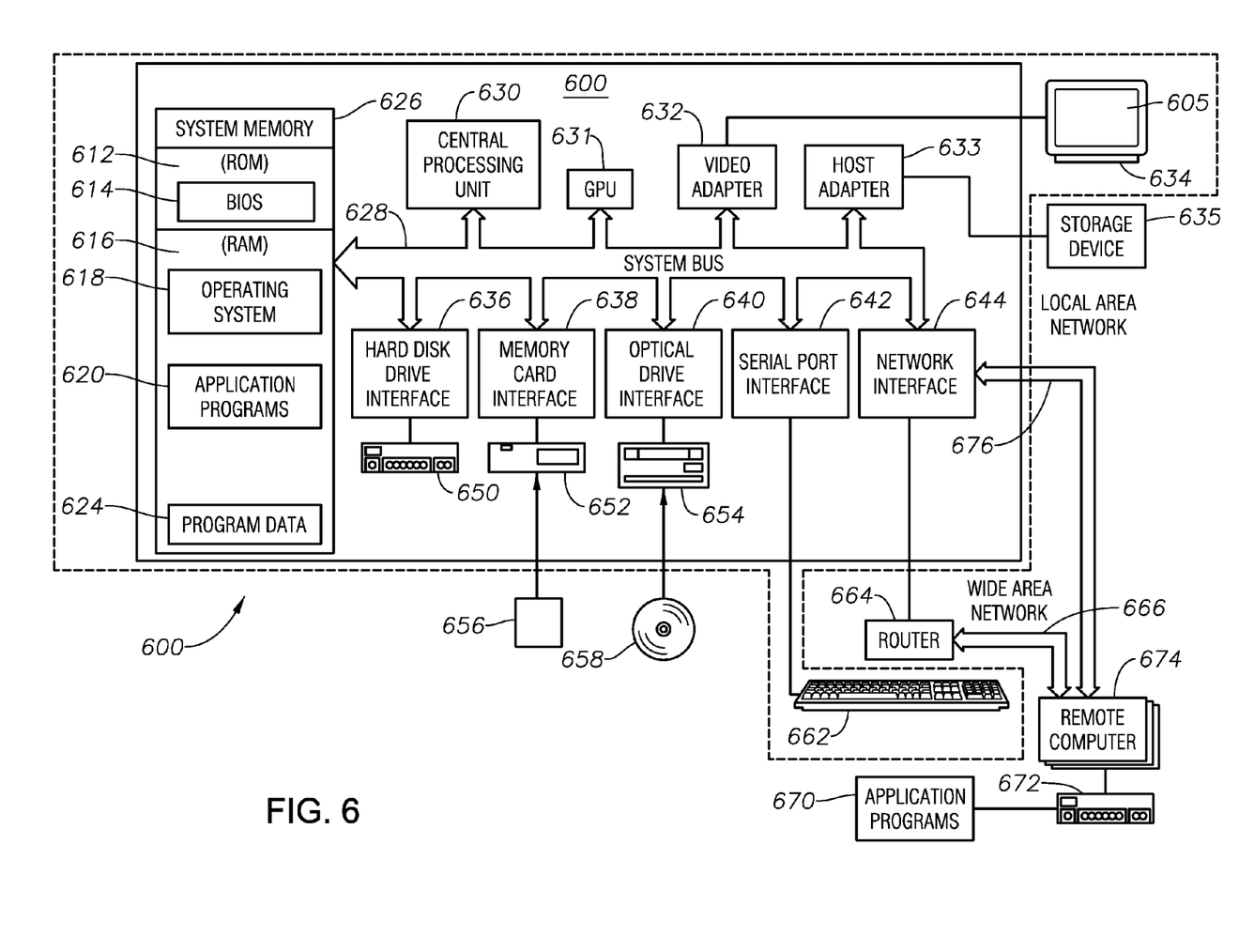
FIG. 6 illustrates a schematic diagram of a computing system in which the various technologies described herein may be incorporated and practiced.
Figure 7:
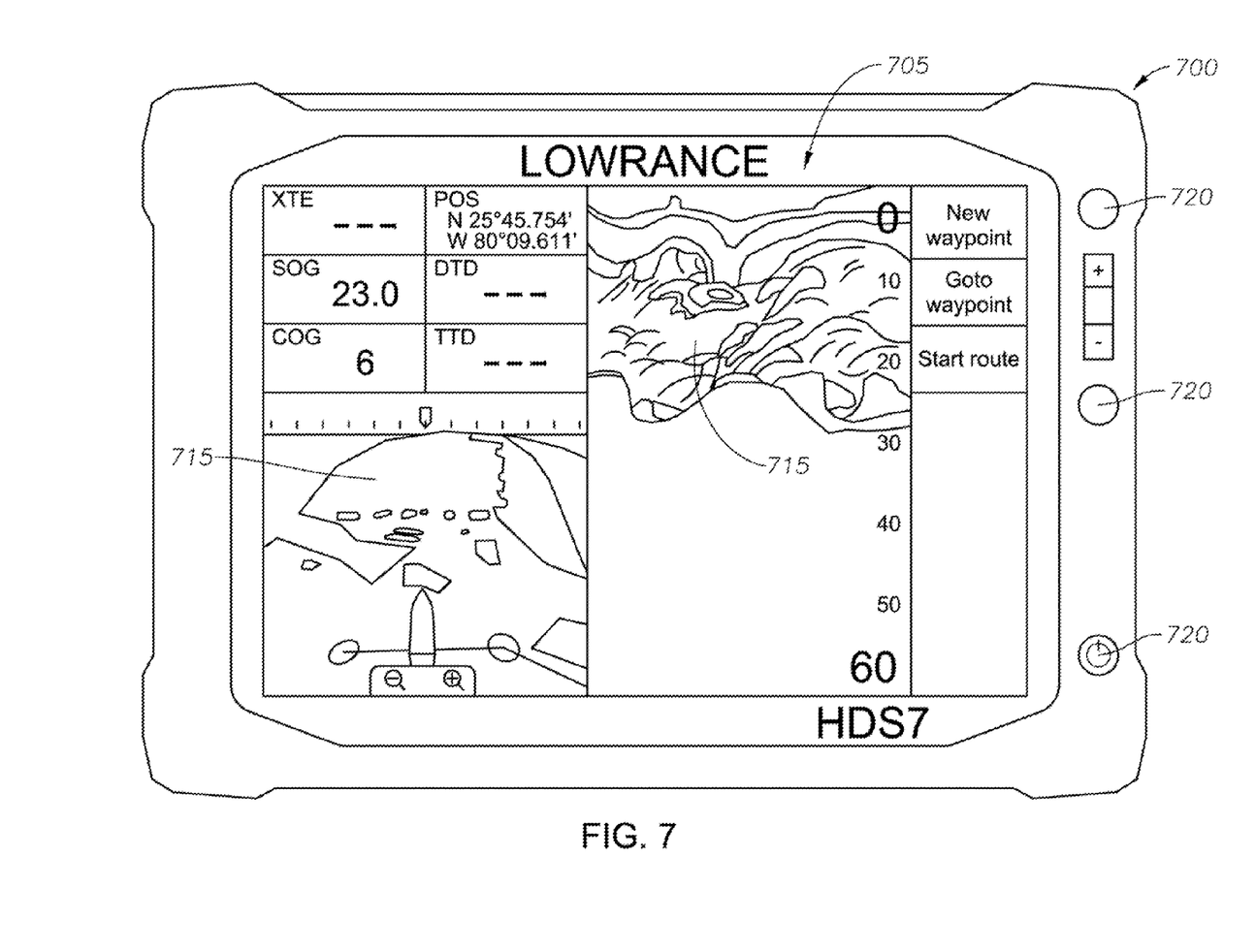
FIG. 7 illustrates a schematic of a marine electronics device in accordance with implementations of various techniques described herein.

FIG. 1 illustrates a flow diagram of a method 100 for analyzing data recorded during a fishing trip in accordance with implementations of various techniques described herein. In one implementation, method 100 may be performed by a computer system 600, including a smart phone, marine electronics device 700 or cloud system. It should be understood that while method 100 indicates a particular order of execution of operations, in some implementations, certain portions of the operations might be executed in a different order, and on different systems. Further, in some implementations, additional operations or steps may be added to the method 100. Likewise, some operations or steps may be omitted.

At block 110, method 100 may receive various data recorded during a fishing trip. The data may be recorded at uniform intervals, or the data may be recorded upon the occurrence of an event.

The data received at block 110 may include Global Positioning System (GPS) data or other location data (also known as spatial data) recorded during a fishing trip. The location data may be time series data, i.e., the location data may include timestamps. The location data may be received in real time during a fishing trip, or after a fishing trip has been completed. In one implementation, the location data may be recorded by a GPS receiver in a marine electronics device 700, a GPS receiver in a smart phone, or a GPS receiver connected to a marine electronics device 700. The location data may be a series of locations travelled by a vessel during a fishing trip, and may include the time at which the vessel was at each location in the series of locations. The location data may also include waypoints recorded during a fishing trip.

The data received at block 110 may include speed and engine data. This data may be recorded using sensors on the vessel or in the motors. The speed and engine data may be time series data, i.e., the speed and engine data may include timestamps. The speed and engine data may be received at regular intervals during a fishing trip. For example, every two seconds, data containing the speed and engine data may be received. The speed and engine data may be received whenever there is a change in the speed and engine data. In one implementation, speed data may be calculated using location data and timestamps corresponding to the location data.

The data received at block 110 may include sonar data. Sonar data may also be described as sounder data or fish finder data. The sonar data may be time series data, i.e., the sonar data may include timestamps. Sonar data may include information regarding the location or depth of fish in the water, the size of any detected fish, any other objects in the water and the depth of the water. Sonar data may be measurements of reflected sound waves. Sonar data may be captured using a transducer attached to a vessel and recorded using a marine electronics device 900.

The data received at block 110 may include fishing data recorded during a fishing trip. The fishing data may be time series data, i.e., the fishing data may include timestamps. The fishing data may be automatically captured using a wearable device 500, further described in more detail in FIG. 5, or entered using buttons on the wearable device. Alternatively, the fishing data may be manually entered into a computer system 600, such as a marine electronics device 700 or a smart phone. Fishing data may include a record of casts made, types of casts made, total number of casts made, bites, catches, types of caught fish, weight of caught fish, length of caught fish or other data related to fishing. For example, when a fisherman casts, a wearable device 500 worn by the fisherman may detect motion corresponding to a cast. The wearable device 500 may then automatically record fishing data describing that a cast has occurred, the type of cast, a timestamp corresponding to the cast, and the location of the cast.

Figure 5:
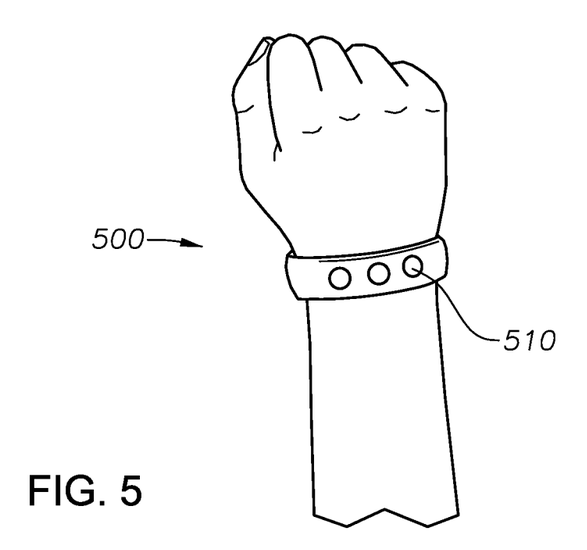
FIG. 5 illustrates a wearable device in accordance with implementations of various techniques described herein.

At block 120, method 100 may analyze the received time series data and determine periods during the trip during which the fishermen was running, finding fish, fishing, trolling, anchored, drifting, or any other fishing activities. In one implementation, method 100 may use data mining techniques, such as clustering, to automatically determine the time periods. In another implementation, the time periods may be manually entered by a fisherman. For example, when a fisherman begins trolling, the fisherman may make a selection using a marine electronics device 700 to indicate that the fisherman is beginning trolling. Then, when the fisherman finishes trolling, the fisherman may make another selection using the marine electronics device 700 to indicate that the fisherman is no longer trolling. In another example, the fisherman may press a button on a wearable device 500, make a gesture captured by the wearable device or say a voice command to indicate the beginning and ending of a fishing activity.

Using location data and speed and engine data, method 100 may automatically determine time periods during a fishing trip that a fisherman was running. For example, method 100 may use location information or speed and engine data to detect time periods where a vessel is traveling above a predefined speed, e.g., 30 mph. Those time periods may then be recorded as time periods spent running during a fishing trip. Running may include traveling to and from a fishing location.

Method 100 may automatically determine time periods during which a fisherman is finding fish. The time periods for finding fish may be detected using speed and engine data, sonar data and by examining activity prior to the time period spent finding fish. For example, method 100 may detect that a fisherman was running and then speed was suddenly reduced. The reduction in speed may correspond to a time period spent finding fish. While finding fish, a fisherman may reduce speed whenever the sonar data indicates that a large number of fish are nearby. In another example, method 100 may determine time periods during which a fisherman is finding fish by detecting time periods during which the speed is reduced when sonar data indicates an increase in the number of fish nearby.

Method 100 may automatically determine time periods spent fishing. Time periods spent fishing may be detected using fishing data, speed and engine data, sonar data and location data. For example, the wearable device 500 may be used to detect casts. At block 120, method 100 may detect time periods in which a fisherman was repeatedly casting. The time periods during which casts are being made may be recorded as time periods spent fishing.

Using location data and speed and engine data, method 100 may automatically determine time periods during a fishing trip that a fisherman was trolling. For example, method 100 may determine that during specific time periods during a fishing trip, a vessel is moving at a consistent, predetermined low speed. Alternately, a fisherman may manually enter times corresponding to the beginning and end of a time period spent trolling, or the fisherman may make a selection on a marine electronics device indicating the beginning and end of a time period spent trolling.

At block 130, method 100 may determine an amount of time corresponding to each time period determined at block 120. Method 100 may determine the total amount of time that elapsed during each determined time period in a fishing trip. Method 100 may also calculate the total amount of time spent on an activity. For example, if method 100 determined at block 120 that three time periods corresponding to fishing occurred during a fishing trip, method 100 may then determine at block 130 an amount of time corresponding to each of the three time periods. Method 100 may also determine at block 130 the sum of the amounts of time corresponding to the three time periods. The amounts of time may be recorded as an amount of time or a percentage of total trip time. For example, method 100 may record that twenty three percent of a fishing trip was spent fishing, thirty five percent of the fishing trip was spent running, and forty two percent of the fishing trip was spent finding fish.

At block 140, method 100 may determine locations corresponding to the time periods determined at block 120. Method 100 may determine the locations in which each activity was performed. For example, at block 140 method 100 may determine the locations where a fisherman was fishing, running, and finding fish during a fishing trip. Method 100 may use the time periods determined at block 120 and time series location data, e.g., GPS data, received at block 110 to determine locations corresponding to the time periods. The locations may be a path traveled by a fisherman or fishing vessel during a fishing trip.

Figure 2:
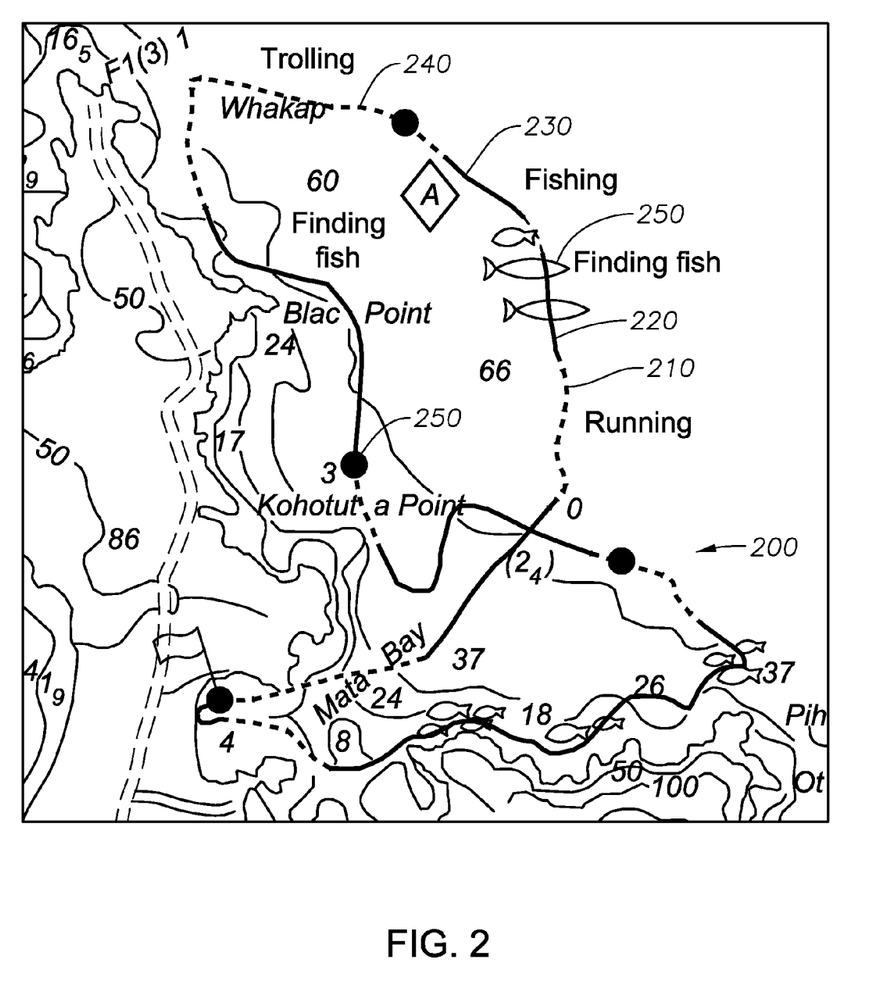
FIG. 2 illustrates a display of activities that occurred during a fishing trip in accordance with implementations of various techniques described herein.
Figure 3:
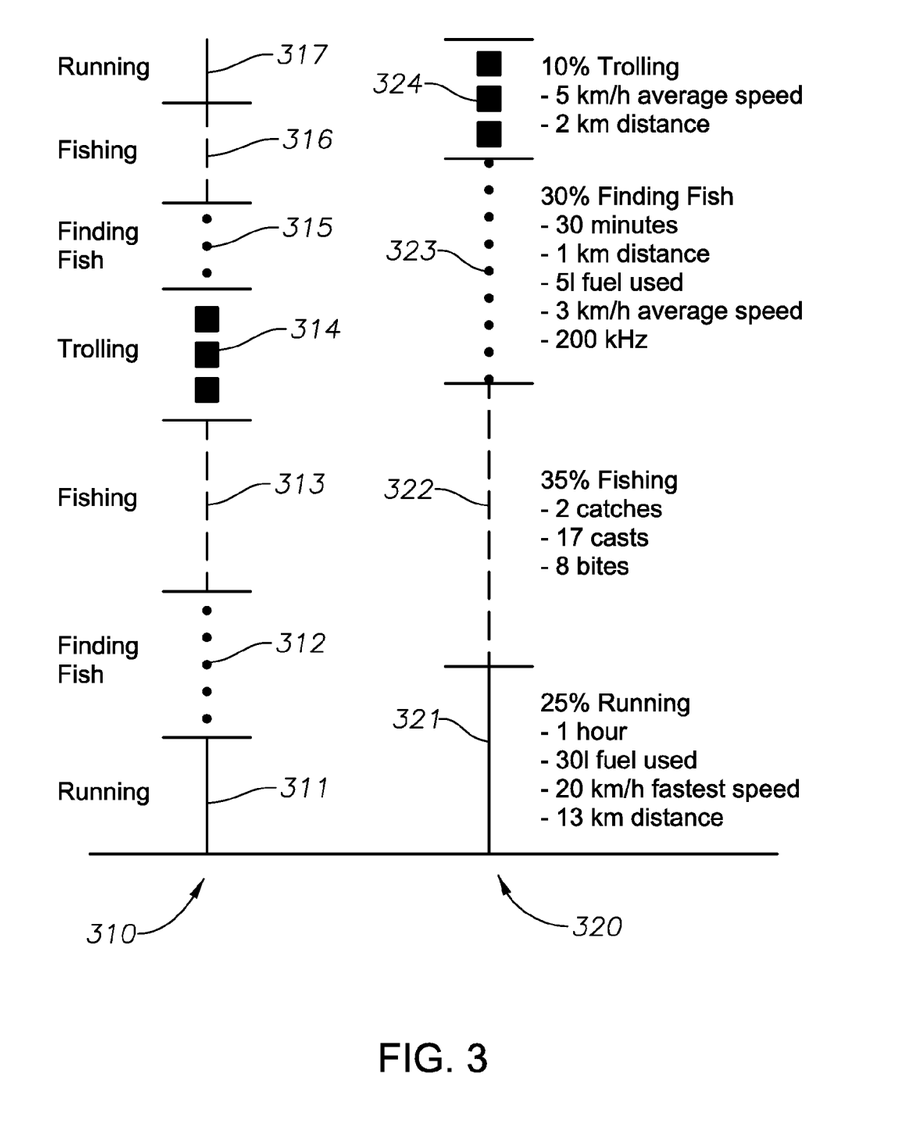
FIG. 3 illustrates a graphical display of activities that occur during a fishing trip in accordance with implementations of various techniques described herein.
Figure 4:
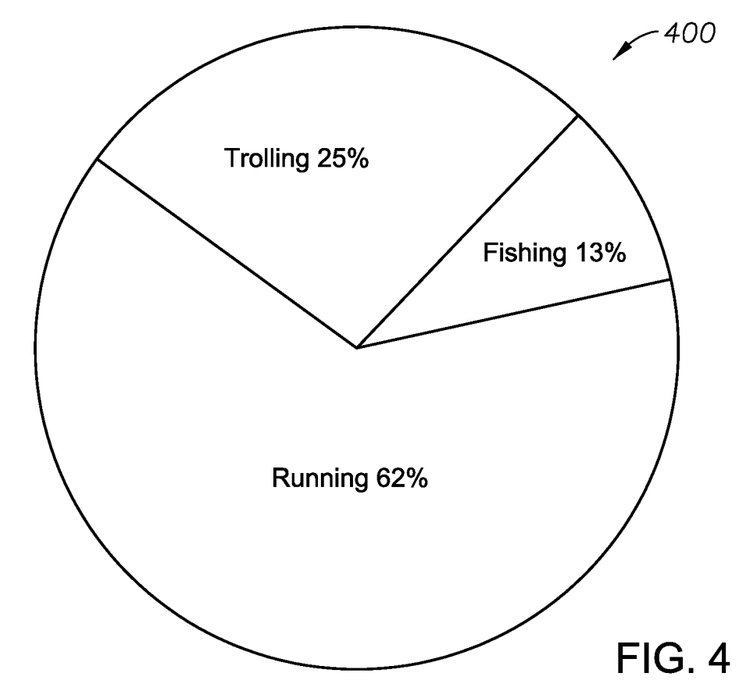
FIG. 4 illustrates a chart display of activities that occur during a fishing trip in accordance with implementations of various techniques described herein.

At block 150, method 100 may display the activities, locations of the activities, and time spent performing the activities as a map, chart, graph, or text. FIGS. 2, 3 and 4 provide examples of displays that may be created using method 100. The method may also transmit or store the data determined at blocks 120, 130 and 140. For example, a database may be created that details the activities that occurred during a fishing trip, the locations of those activities, and the times corresponding to each activity.

At block 160, method 100 may display additional information corresponding to the time periods. For a time period that corresponds to fishing, the additional information may include a number of casts, catches, bites, a cast rate, an average weight of caught fish, or other fishing data. For a time period that corresponds to running, the additional information may include an amount of fuel used, a top speed, and an average speed. In any time period, the additional information may include a percentage of time spent on that type of activity. For example, for a time period that corresponds to finding fish, the additional information may include the percentage of time spent finding fish out of the entire duration of a fishing trip. Examples of additional information that may be displayed are included in FIG. 3.

In one implementation, blocks 110-160 may be performed on a marine electronics device or smartphone. In a second implementation, blocks 110-160 may be performed by a cloud software service. For example, GPS data, speed and engine data, sonar data, and fishing data may be collected using a marine electronics device 700 and transmitted to a cloud software service. The cloud software service may then determine the time periods and activities during the fishing trip, and display the time periods. The cloud software service may also share the display or data with other users of the cloud software service.

FIG. 2 illustrates a display of activities that occurred during a fishing trip in accordance with implementations of various techniques described herein. The display may be displayed on a marine electronics device as described in FIG. 7, a computer as described in FIG. 6, a smartphone device, or any other display device.

In the illustrated display, a map is shown with a recorded path of a fishing trip. Fishing activities determined using method 100 at block 120 may be displayed along the path. The path 200 may have been recorded by a positioning system on a marine vessel, or by a smartphone or other device used by a fisherman. The path 200 may be drawn using a series of coordinates recorded by a positioning system. The path 200 may be drawn to represent fishing activities with patterns, colors, or any other method to display fishing activities on the path 200. In FIG. 2, the illustrated display uses alternating dotted lines and solid lines to display the locations of different activities along the path 200. In another implementation, the path 200 may be a first color or pattern when the activity is running, a second color or pattern when the activity is fishing, a third color or pattern when the activity is trolling, and a fourth color or pattern when the activity is finding fish.

Segment 210, which is a segment of the path 200 drawn using a dotted line, may be used to indicated that the fisherman was running. Segment 220, shown as a solid line, may be used to indicate that the fisherman was finding fish. At segment 230, the fisherman was fishing. Segment 240 may be used to indicate that the fisherman was trolling.

The path may contain icons 250 to indicate the location of a recorded event. For instance, these icons 250 may indicate the location of a catch, a bite, a saved location/waypoint, or any other event that may occur during a fishing trip. The illustrated icons 250 in FIG. 2 are either black dots or drawings of fish, but any symbol may be used as an icon 250.

In one implementation, a user may select a segment on the path or an icon 240 and additional information regarding the selection will be displayed. If a segment is selected, the additional information may include statistics corresponding to the segment. For example, if segment 230 is selected, a number of casts, bites and caught fish, and a cast to catch ratio corresponding to the segment 230 may be displayed. In another example, if segment 210 is selected, the fuel used, top speed and average speed corresponding to the segment 210 may be displayed.

In another implementation, each segment displayed in FIG. 200 may include multiple colors to display statistics within the segment. For example, in a running segment, portions of the running segment in which a vessel's speed was slow may be colored green, and portions where the vessel's speed was higher may be colored red. In a second example, in a fishing segment, portions of the segment in which the cast rate was low may be colored red, and portions of the segment in which the cast rate was high may be colored green.

FIG. 3 illustrates a graphical display of activities that occurred during a fishing trip in accordance with implementations of various techniques described herein. Graph 310 displays fishing activities in the order that they occurred during a fishing trip. During the fishing trip illustrated in graph 310, the fisherman is shown as first running at segment 311, then finding fish at segment 312, then fishing at segment 313, then trolling at segment 314, then finding fish at segment 315, then fishing at segment 316 and finally running again at segment 317. The length of each segment in graph 310 may be related to the amount of time that elapsed during the activity represented in the segment.

Graph 320 displays the total time spent on activities during a fishing trip. For example, segment 321 shows the total time spent running during a fishing trip, segment 322 shows the total time spent fishing, segment 323 shows the total time spent finding fish and segment 324 shows the total time spent trolling. Segment 321 shows the combined data of the two segments during the fishing trip in which the fisherman was running, i.e., segment 321 shows the combined data of segments 311 and 317. During the fishing trip described in FIG. 3, a fisherman spent twenty five percent of the trip running, thirty five percent of the trip fishing, thirty percent of the trip finding fish and ten percent of the trip trolling.

Graphs 310 and 320 may also display additional information regarding the segments. In one implementation, the additional information may be displayed when a user selects a segment. In another implementation, the additional information may be displayed adjacent to one or more segments whenever the graphs 310 and 320 are displayed. The illustrated graph 320 includes additional information describing segments 321, 322, 323 and 324. At segment 321, the additional information includes statistics describing the total amount of time spent running, the total amount of fuel used, the highest speed, and the total distance traveled for all of the running segments in the entire fishing trip. At segment 322, the additional information describes the total number of catches, casts, and bites for all of the fishing segments in the entire fishing trip. At segment 323, the additional information includes the total distance traveled, the total amount of fuel used, the average speed and average frequency used for all of the finding fish segments in the entire fishing trip. At segment 324, the additional information includes the average speed and the total distance traveled for all the trolling segments in the entire fishing trip. Additional information may also be included for individual segments shown on graph 310. For example, the number of casts, catches, or bites that occurred during segment 313 may be displayed.

In FIG. 3, the segments in graphs 310 and 320 are drawn using dotted lines, solid lines, and lines composed of circles and squares to represent different activities. Other patterns or designs are also contemplated to represent the different activities. In another implementation, the segments in graphs 310 and 320 may be a first color when the activity is running, a second color when the activity is fishing, a third color when the activity is trolling, and a fourth color when the activity is finding fish.

FIG. 4 illustrates a chart display of activities that occur during a fishing trip in accordance with implementations of various techniques described herein.

In FIG. 4, activities that occurred during a fishing trip are displayed using a pie chart 400. The chart 400 may be drawn using data determined from method 100 at blocks 120 and 130. In one implementation, the pie chart 400 displays the same information as graph 320 but in a pie chart format. In another implementation, a user may select a section of the chart 400 and additional information regarding the selection will be displayed. For example, if the running section of the chart 400 is selected, the total amount of time spent running, the total amount of fuel used, the highest speed, and the total distance traveled for all of the running segments in the entire fishing trip may then be displayed.

Wearable Device

FIG. 5 illustrates a wearable device 500 in accordance with various implementations described herein. The wearable device 500 may be worn around a fisherman's arm or wrist. In one implementation, the wearable device 500 may be in the shape of a band. The wearable device 500 may be made of a combination of plastics and rubbers, or of any other synthetic material. The wearable device 500 may also be waterproof. The wearable device 500 may include one or more buttons 510. The wearable device may contain a display. Although the wearable device is described as a band, the wearable device may be a watch, pair of eyeglasses, or any other device that can be worn or attached to the body, clothing or attached to fishing equipment.

The wearable device 500 may include a computer and one or more sensors, including a motion sensor. The sensors in the wearable device 500 may include one or more accelerometers, gyroscopes, muscle activity sensors, any other motion sensor, or any combination of motion sensors. The wearable device 500 may include one or more microphones, or any other audio sensor, for recording audio data. The computer is described in more detail in FIG. 6. In one implementation, the computer may be loaded with software to determine time periods for a fishing activity.

The wearable device 500 may use any combination of microphones, motion sensors and the buttons 510 to detect fishing events. For example, after a fishing cast is performed, the wearable device 500 may determine that the cast has occurred using a motion sensor. In a second example, the one or more buttons 510 may be used to input the occurrence of a catch. In a third example a user may press a button 510 to input the occurrence of a catch, and then may press the same or different button 510 to input the weight of the caught fish. In a fourth example, after a bite, a user may give a voice command by saying "bite." The voice command may then be detected using a microphone.

The wearable device 500 may include wireless technology, such as Bluetooth, Wi-Fi, cellular technology such as GSM or CDMA, satellite communication, or any other wireless technology. In one implementation, the wearable device 500 may be connected wirelessly to a marine electronics device 700. Although the wearable device 500 is described as being wirelessly connected to a marine electronics device 700, it should be understood that the wearable device 500 may be connected to any computer system 600, including a portable computer system, a smart phone device, a remote server, a cloud server and the like.

The marine electronics device 700 or a computer system 600, including a smart phone, may record additional data, such as location, which may be recorded using GPS technology, weather, sonar, speed and engine data or other data. The data from the marine electronics device 700 or computer system 600 and the wearable device 500 may then be combined to provide comprehensive data regarding a fishing trip. The combined data may then be transmitted to a remote server or cloud software service. The data may be used as input for method 100. In one implementation, the combined data may be transmitted to a smart phone device, which then transmits the data to a remote server or a cloud software service. In another implementation, the combined data may be transmitted to a data logging device, which may then transmit the combined data at a later time. In yet another implementation, the data from the wearable device 500 may be transmitted to a remote server or cloud software service via a smart phone without using the marine electronics device 700. In another implementation, the data from the wearable device may be transmitted directly to a cloud software service.

Computing System

Implementations of various technologies described herein may be operational with numerous general purpose or special purpose computing system environments or configurations. Examples of well known computing systems, environments, and/or configurations that may be suitable for use with the various technologies described herein include, but are not limited to, personal computers, server computers, hand-held or laptop devices, multiprocessor systems, microprocessor-based systems, set top boxes, programmable consumer electronics, network PCs, minicomputers, mainframe computers, smart phones, tablets, wearable computers, cloud computing systems, virtual computers, and the like.

The various technologies described herein may be implemented in the general context of computer-executable instructions, such as program modules, being executed by a computer. Generally, program modules include routines, programs, objects, components, data structures, etc. that performs particular tasks or implement particular abstract data types. Further, each program module may be implemented in its own way, and all need not be implemented the same way. While program modules may all execute on a single computing system, it should be appreciated that, in some implementations, program modules may be implemented on separate computing systems or devices adapted to communicate with one another. A program module may also be some combination of hardware and software where particular tasks performed by the program module may be done either through hardware, software, or both.

The various technologies described herein may be implemented in the context of marine electronics, such as devices found in marine vessels and/or navigation systems. Ship instruments and equipment may be connected to the computing systems described herein for executing one or more navigation technologies. As such, the computing systems may be configured to operate using sonar, radar, GPS and like technologies.

The various technologies described herein may also be implemented in distributed computing environments where tasks are performed by remote processing devices that are linked through a communications network, e.g., by hard-wired links, wireless links, or combinations thereof. In a distributed computing environment, program modules may be located in both local and remote computer storage media including memory storage devices.

FIG. 6 illustrates a computer system 600 into which implementations of various technologies and techniques described herein may be implemented. Computing system 600 may be a conventional desktop, a handheld device, a wearable device, a controller, a personal digital assistant, a server computer, an electronic device/instrument, a laptop, a tablet, or part of a navigation system, marine electronics, or sonar system. It should be noted, however, that other computer system configurations may be used.

The computing system 600 may include a central processing unit (CPU) 630, a system memory 626 and a system bus 628 that couples various system components including the system memory 626 to the CPU 630. Although only one CPU 630 is illustrated in FIG. 6, it should be understood that in some implementations the computing system 600 may include more than one CPU 630.

The CPU 630 can include a microprocessor, a microcontroller, a processor, a programmable integrated circuit, or a combination thereof. The CPU 630 can comprise an off-the-shelf processor such as a Reduced Instruction Set Computer (RISC), including an Advanced RISC Machine (ARM) processor, or a Microprocessor without Interlocked Pipeline Stages (MIPS) processor, or a combination thereof. The CPU 630 may also include a proprietary processor. The CPU may include a multi-core processor.

The GPU 631 may be a microprocessor specifically designed to manipulate and implement computer graphics. The CPU 630 may offload work to the GPU 631. The GPU 631 may have its own graphics memory, and/or may have access to a portion of the system memory 626. As with the CPU 630, the GPU 631 may include one or more processing units, and each processing unit may include one or more cores.

The CPU 630 may provide output data to a GPU 631. The GPU 631 may generate graphical user interfaces that present the output data. The GPU 631 may also provide objects, such as menus, in the graphical user interface. A user may provide inputs by interacting with the objects. The GPU 631 may receive the inputs from interaction with the objects and provide the inputs to the CPU 630. In one implementation, the CPU 630 may perform the tasks of the GPU 631. A video adapter 632 may be provided to convert graphical data into signals for a monitor 634. The monitor 634 includes a screen 605. The screen 605 can be sensitive to heat or touching (now collectively referred to as a "touch screen"). In one implementation, the computer system 600 may not include a monitor 634.

The system bus 628 may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 626 may include a read only memory (ROM) 612 and a random access memory (RAM) 616. A basic input/output system (BIOS) 614, containing the basic routines that help transfer information between elements within the computing system 600, such as during start-up, may be stored in the ROM 612. The computing system may be implemented using a printed circuit board containing various components including processing units, data storage memory, and connectors.

Certain implementations may be configured to be connected to a GPS and/or a sonar system. The GPS and/or sonar system may be connected via the network interface 644 or Universal Serial Bus (USB) interface 642. In one implementation, the computing system 600, the monitor 634, the screen 605 and buttons may be integrated into a console.

The computing system 600 may further include a hard disk drive 636 for reading from and writing to a hard disk 650, a memory card reader 652 for reading from and writing to a removable memory card 656 and an optical disk drive 654 for reading from and writing to a removable optical disk 658, such as a CD ROM, DVD ROM or other optical media. The hard disk drive 650, the memory card reader 652 and the optical disk drive 654 may be connected to the system bus 628 by a hard disk drive interface 636, a memory card interface 638 and an optical drive interface 640, respectively. The drives and their associated computer-readable media may provide nonvolatile storage of computer-readable instructions, data structures, program modules and other data for the computing system 600.

Although the computing system 600 is described herein as having a hard disk, a removable memory card 656 and a removable optical disk 658, it should be appreciated by those skilled in the art that the computing system 600 may also include other types of computer-readable media that may be accessed by a computer. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, including a Solid State Disk (SSD), CD-ROM, digital versatile disks (DVD), or other optical storage, magnetic cassettes, magnetic tape, magnetic disk storage or other magnetic storage devices, or any other medium which can be used to store the desired information and which can be accessed by the computing system 600. Communication media may embody computer readable instructions, data structures, program modules or other data in a modulated data signal, such as a carrier wave or other transport mechanism and may include any information delivery media. By way of example, and not limitation, communication media may include wired media such as a wired network or direct-wired connection, and wireless media such as acoustic, RF, infrared and other wireless media. The computing system 600 may also include a host adapter 633 that connects to a storage device 635 via a small computer system interface (SCSI) bus, a Fiber Channel bus, an eSATA bus, or using any other applicable computer bus interface. The computing system 600 can also be connected to a router 664 to establish a wide area network (WAN) 666 with one or more remote computers 674. The router 664 may be connected to the system bus 628 via a network interface 644. The remote computers 674 can also include hard disks 672 that store application programs 670.

In another implementation, the computing system 600 may also connect to one or more remote computers 674 via local area network (LAN) 676 or the WAN 666. When using a LAN networking environment, the computing system 600 may be connected to the LAN 676 through the network interface or adapter 644. The LAN 676 may be implemented via a wired connection or a wireless connection. The LAN 676 may be implemented using Wi-Fi technology, cellular technology, or any other implementation known to those skilled in the art. The network interface 644 may also utilize remote access technologies (e.g., Remote Access Service (RAS), Virtual Private Networking (VPN), Secure Socket Layer (SSL), Layer 2 Tunneling (L2T), or any other suitable protocol). These remote access technologies may be implemented in connection with the remote computers 674. It will be appreciated that the network connections shown are exemplary and other means of establishing a communications link between the computer systems may be used. The network interface 644 may also include digital cellular networks, Bluetooth, or any other wireless network interface.

A number of program modules may be stored on the hard disk 650, memory card 656, optical disk 658, ROM 612 or RAM 616, including an operating system 618, one or more application programs 620, program data 624, and a database system. The one or more application programs 620 may contain program instructions configured to perform method 100 according to various implementations described herein. The operating system 618 may be any suitable operating system that may control the operation of a networked personal or server computer, such as Windows® XP, Mac OS® X, Unix-variants (e.g., Linux® and BSD®), Android®, iOS®, and the like.

A user may enter commands and information into the computing system 600 through input devices such as a keyboard 662 and pointing device. Other input devices may include a microphone, joystick, game pad, satellite dish, scanner, user input button, wearable device, or the like. These and other input devices may be connected to the CPU 630 through a USB interface 642 coupled to system bus 628, but may be connected by other interfaces, such as a parallel port, Bluetooth, or a game port. A monitor 605 or other type of display device may also be connected to system bus 628 via an interface, such as a video adapter 632. The monitor 605 may be used to display activity displays as described in FIGS. 2-4. In addition to the monitor 634, the computing system 600 may further include other peripheral output devices such as speakers and printers.

Marine Electronics Device

FIG. 7 illustrates a schematic diagram of a marine electronics device 700 in accordance with various implementations described herein. The marine electronics device 700 includes a screen 705. In certain implementations, the screen 705 may be sensitive to touching by a finger. In other implementations, the screen 705 may be sensitive to the body heat from the finger, a stylus, or responsive to a mouse. The device 700 may display marine electronic data 715. The marine electronic data types 715 may include chart data, radar data, sonar data, steering data, dashboard data, navigation data, fishing data, and the like. The marine electronic data types may include activity displays, including those illustrated in FIGS. 2, 3 and 4. The marine electronics device 700 may also include a plurality of buttons 720, which may be either physical buttons or virtual buttons, or a combination thereof. The marine electronics device 700 may include one or more microphones, or may receive audio data recorded by one or more microphones. The audio data may be analyzed by the marine electronics device 700 to detect voice commands, which may be used as input by the marine electronics device 700. The marine electronics device 700 may receive input through a screen 705 sensitive to touch, buttons 720, or voice commands.

While the foregoing is directed to implementations of various techniques described herein, other and further implementations may be devised without departing from the basic scope thereof, which may be determined by the claims that follow.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A non-transitory computer-readable medium having stored thereon a plurality of computer-executable instructions which, when executed by a computer, cause the computer to:

receive data recorded during a fishing trip, wherein the fishing trip is by one or more fisherman using a vessel on a body of water, wherein the data comprises at least fishing log data that is sensed and recorded by at least a wearable device or the fishing log data that is sensed and recorded by at least the wearable device in combination with at least one of location data, speed and engine data, or sonar data, wherein the wearable device is worn by a user and comprises one or more integrated sensors, and wherein the data sensed and recorded by the wearable device comprises a record of at least one of catches, casts, or bites;

determine, based on the received data, at least three different types of fishing activity and a corresponding time period for each determined type of fishing activity during the fishing trip, wherein the types of fishing activity include at least three of running, finding fish, trolling, or fishing, wherein at least one of the determined three types of fishing activity is fishing, wherein determining a time period for fishing comprises using at least the fishing log data that is sensed and recorded by the wearable device, wherein a time period for running corresponds to a time period during the fishing trip where the vessel is traveling to or from a location on the body of water, wherein a time period for finding fish corresponds to a time period during the fishing trip where the one or more fisherman is attempting to locate fish, wherein the time period for fishing corresponds to a time period during the fishing trip where the one or more fisherman is attempting to catch fish, wherein a time period for trolling corresponds to a time period during the fishing trip where the one or more fisherman is traveling at a consistent, predetermined low speed;

determine, based on the received data, one or more portions of a route of the fishing trip that correspond to each of the determined at least three types of fishing activity such that the corresponding type of fishing activity was performed at one or more locations corresponding to the one or more portions of the route; and cause a screen of a marine electronic device to display the one or more portions of the route that correspond to each of the determined at least three types of fishing activity in relation to the route of the fishing trip such that the one or more portions of the route are distinct from at least any remaining portions of the route.

2. The non-transitory computer-readable medium of claim 1, wherein both the data sensed and recorded by the wearable device and the location data are time series data.

3. The non-transitory computer-readable medium of claim 1, wherein a start period and end period of a time period corresponding to a type of fishing activity is indicated by a gesture from the user.

4. The non-transitory computer-readable medium of claim 3, wherein the gesture from the user is detected automatically by the wearable device.

5. The non-transitory computer-readable medium of claim 1, wherein the computer-executable instructions further cause the computer to:

cause the screen of the marine electronic device to display the determined at least three different types of fishing activity on a chart or graph along with a time ratio of a total time for the type of fishing activity to a total time of the fishing trip.

6. The non-transitory computer-readable medium of claim 1, wherein the computer-executable instructions further cause the computer to:

cause display of one or more portions of the route corresponding to the fishing activity of running using a first color or pattern;

cause display of one or more portions of the route corresponding to the fishing activity of finding fish using a second color or pattern;

cause display of one or more portions of the route corresponding to the fishing activity of trolling using a third color or pattern; and cause display of one or more portions of the route corresponding to the fishing activity of fishing using a fourth color or pattern.

7. The non-transitory computer-readable medium of claim 1, wherein the computer-executable instructions further cause the computer to:

determine one or more time periods for the fishing activity of running using at least one of location data or speed and engine data;

determine one or more time periods for the fishing activity of finding fish by using at least one of speed and engine data or sonar data;

determine one or more time periods for the fishing activity of fishing by using at least one of speed and engine data, sonar data, location data, or fishing log data; and determine one or more time periods for the fishing activity of trolling by using at least one of speed and engine data or data received from a user interface.

8. The non-transitory computer-readable medium of claim 1, wherein the computer-executable instructions further cause the computer to determine one or more time periods during the fishing trip for each of the fishing activity of running, the fishing activity of finding fish, and the fishing activity of fishing.

9. A non-transitory computer-readable medium having stored thereon a plurality of computer-executable instructions which, when executed by a computer, cause the computer to:
receive data recorded during a fishing trip, wherein the fishing trip is by one or more fisherman using a vessel on a body of water, wherein the data comprises at least fishing log data that is sensed and recorded by at least a wearable device or the fishing log data that is sensed and recorded by at least the wearable device in combination with at least one of location data, speed and engine data, or sonar data, wherein the wearable device is worn by a user and comprises one or more integrated sensors, and wherein the data sensed and recorded by the wearable device comprises a record of at least one of catches, casts, or bites;
determine, based on the received data, at least three different types of fishing activity and a corresponding time period for each determined type of fishing activity during the fishing trip, wherein the types of fishing activity include at least three of running, finding fish, trolling, or fishing, wherein at least one of the determined three types of fishing activity is fishing, wherein determining a time period for fishing comprises using at least the fishing log data that is sensed and recorded by the wearable device;
wherein a time period for running corresponds to a time period during the fishing trip where the vessel is traveling to or from a location on the body of water,
wherein a time period for finding fish corresponds to a time period during the fishing trip where the one or more fisherman is attempting to locate fish,
wherein the time period for fishing corresponds to a time period during the fishing trip where the one or more fisherman is attempting to catch fish,
wherein a time period for trolling corresponds to a time period during the fishing trip where the one or more fisherman is traveling at a consistent, predetermined low speed; and
cause a screen of a marine electronic device to display the determined at least three different types of fishing activity on a chart or graph along with a time ratio of a total time for the type of fishing activity to a total time of the fishing trip.

10. The non-transitory computer-readable medium of claim 9, wherein the sonar data comprises data received by a transducer.

11. The non-transitory computer-readable medium of claim 9, wherein the time ratio of each of the determined types of fishing activity is displayed as a percentage of a pie chart or bar graph.

12. The non-transitory computer-readable medium of claim 9, wherein the computer-executable instructions further cause the computer to cause display of the determined three types of fishing activity by displaying one or more segments of the chart or graph, wherein each of the one or more segments correspond to one of the determined types of fishing activity, and wherein the computer-executable instructions further cause the computer to cause display of statistics corresponding to a determined type of fishing activity based on a selection of a displayed segment associated with the determined type of fishing activity.

13. The non-transitory computer-readable medium of claim 9, wherein the computer-executable instructions further cause the computer to cause display of one or more locations corresponding to each of the determined at least three types of fishing activity on a map.

14. The non-transitory computer-readable medium of claim 9, wherein the computer-executable instructions further cause the computer to:
determine one or more time periods for the fishing activity of running using at least one of location data or speed and engine data;
determine one or more time periods for the fishing activity of finding fish by using at least one of speed and engine data or sonar data;
determine one or more time periods for the fishing activity of fishing by using at least one of speed and engine data, sonar data, location data, or fishing log data; and
determine one or more time periods for the fishing activity of trolling by using at least one of speed and engine data or data received from a user interface.

15. The non-transitory computer-readable medium of claim 9, wherein the computer-executable instructions further cause the computer to determine one or more time periods during the fishing trip for each of the fishing activity of running, the fishing activity of finding fish, and the fishing activity of fishing.

16. A non-transitory computer-readable medium having stored thereon a plurality of computer-executable instructions which, when executed by a computer, cause the computer to:
receive data recorded during a fishing trip, wherein the fishing trip is by one or more fisherman using a vessel on a body of water, wherein the data comprises at least fishing log data that is sensed and recorded by at least a wearable device or the fishing log data that is sensed and recorded by at least the wearable device in combination with at least one of location data, speed and engine data, or sonar data, wherein the wearable device is worn by a user and comprises one or more integrated sensors, and wherein the data sensed and recorded by the wearable device comprises a record of at least one of catches, casts, or bites;
determine, based on the received data, at least three different types of fishing activity and a corresponding time period for each determined type of fishing activity during the fishing trip, wherein the types of fishing activity include at least three of running, finding fish, trolling, or fishing, wherein at least one of the determined three types of fishing activity is fishing, wherein determining a time period for fishing comprises using at least the fishing log data that is sensed and recorded by the wearable device;
wherein a time period for running corresponds to a time period during the fishing trip where the vessel is traveling to or from a location on the body of water,
wherein a time period for finding fish corresponds to a time period during the fishing trip where the one or more fisherman is attempting to locate fish,
wherein the time period for fishing corresponds to a time period during the fishing trip where the one or more fisherman is attempting to catch fish, wherein a time period for trolling corresponds to a time period during the fishing trip where the one or more fisherman is traveling at a consistent, predetermined low speed;

determine, based on the received data, one or more portions of a route of the fishing trip that correspond to each of the determined at least three types of fishing activity such that the corresponding type of fishing activity was performed at one or more locations corresponding to the one or more portions of the route; and cause a screen of a marine electronic device to display the one or more portions of the route that correspond to each of the determined at least three types of fishing activity in relation to the route of the fishing trip such that the one or more portions of the route are distinct from at least any remaining portions of the route.

17. The non-transitory computer-readable medium of claim 16, wherein the computer-executable instructions further cause the computer to:

cause display of one or more portions of the route corresponding to the fishing activity of running using a first color or pattern;

cause display of one or more portions of the route corresponding to the fishing activity of finding fish using a second color or pattern;

cause display of one or more portions of the route corresponding to the fishing activity of trolling using a third color or pattern; and cause display of one or more portions of the route corresponding to the fishing activity of fishing using a fourth color or pattern.

18. The non-transitory computer-readable medium of claim 16, wherein the computer-executable instructions further cause the computer to:

determine one or more time periods for the fishing activity of running using at least one of location data or speed and engine data;

determine one or more time periods for the fishing activity of finding fish by using at least one of speed and engine data or sonar data;

determine one or more time periods for the fishing activity of fishing by using at least one of speed and engine data, sonar data, location data, or fishing log data; and determine one or more time periods for the fishing activity of trolling by using at least one of speed and engine data or data received from a user interface.

19. The non-transitory computer-readable medium of claim 16, wherein the computer-executable instructions further cause the computer to determine one or more time periods during the fishing trip for each of the fishing activity of running, the fishing activity of finding fish, and the fishing activity of fishing.

* * * * *